US005454792A

United States Patent [19]
Tennican et al.

[11] Patent Number: 5,454,792
[45] Date of Patent: Oct. 3, 1995

[54] LINEAR SLIDE VALVE FOR CVC ACCESS

[75] Inventors: Patrick O. Tennican; L. Myles Phipps; Russell A. Michaelsen, all of Spokane, Wash.

[73] Assignee: Hyproteck, Inc., Spokane, Wash.

[21] Appl. No.: 229,004

[22] Filed: Apr. 18, 1994

Related U.S. Application Data

[63] Continuation-in-part of Ser. No. 187,632, Jan. 26, 1994, Pat. No. 5,411,485, and a continuation-in-part of Ser. No. 48,906, Apr. 19, 1993, Pat. No. 5,308,322.

[51] Int. Cl.$^6$ ..................................... A61M 5/19
[52] U.S. Cl. ............................. 604/191; 604/89; 604/249; 137/625.11
[58] Field of Search ........................... 604/83, 87, 88, 604/183, 185, 191, 30, 36, 38, 62, 64, 89, 91, 173, 187, 188, 218, 232, 240, 258, 249; 137/605, 625.11, 625.4; 251/326

[56] References Cited

U.S. PATENT DOCUMENTS

| | | |
|---|---|---|
| 665,192 | 1/1901 | Demarest . |
| 869,702 | 10/1907 | Friend . |
| 1,948,388 | 7/1934 | Liberson ................................. 604/191 |
| 1,977,337 | 10/1934 | Granberg . |
| 2,077,774 | 4/1937 | Rudder . |
| 2,111,572 | 3/1938 | Sall . |
| 2,254,994 | 11/1941 | Butland . |
| 2,642,852 | 6/1953 | Bester . |
| 2,680,455 | 6/1954 | Raiteri . |
| 3,051,174 | 9/1962 | Mandell . |
| 3,254,646 | 6/1966 | Staunt et al. . |
| 3,561,433 | 2/1971 | Kovach . |
| 3,678,959 | 7/1972 | Liposky . |
| 3,955,591 | 5/1976 | Baumann . |
| 3,957,082 | 5/1976 | Fuson et al. . |
| 4,109,653 | 8/1978 | Kozam et al. . |
| 4,367,737 | 1/1983 | Kozam et al. . |
| 4,471,765 | 9/1984 | Strauss et al. . |
| 4,593,717 | 6/1986 | Levasseur . |
| 4,604,093 | 8/1986 | Brown et al. . |
| 4,609,371 | 9/1986 | Pizzino . |
| 4,610,666 | 9/1986 | Pizzino . |
| 4,666,429 | 5/1987 | Stone . |
| 4,758,235 | 6/1988 | Tu . |
| 4,784,157 | 11/1988 | Halls et al. . |
| 4,795,441 | 1/1989 | Bhatt . |
| 4,915,688 | 4/1990 | Bischof et al. . |

(List continued on next page.)

FOREIGN PATENT DOCUMENTS

| | | |
|---|---|---|
| 737249 | of 1966 | Canada . |
| WO92/11044 | of 1992 | WIPO . |

OTHER PUBLICATIONS

"Three Easy Steps to More Convenient Sash", Block Medical, Inc., California (Jun. 1993) Produce Brochure.

*Primary Examiner*—C. Fred Rosenbaum
*Assistant Examiner*—Perry E. Van Over
*Attorney, Agent, or Firm*—Wells, St. John, Roberts, Gregory & Matkin

[57] ABSTRACT

A catheter access system comprises and integrally molded base sheet which forms first and second opposed slide valve walls. The slide valve walls form an upwardly-open longitudinal valley therebetween. An elongated sliding member is received for slidable movement within the longitudinal valley. A plurality of slide valve inlet ports extend through the first slide valve wall. A slide valve outlet port extends through the second slide valve wall. A plurality of syringes are mounted on the integrally-molded base sheet for fluid communication with the slide valve inlet ports. The elongated sliding member is movable between a plurality of discrete longitudinal positions to individually select slide valve inlet ports for connection to the slide valve outlet port. The sliding member has a plurality of sliding member passageways corresponding to the slide valve inlet ports. The passageways are positioned so that they each connect between their corresponding slide valve inlet ports and the slide valve outlet port at the different discrete longitudinal positions of the elongated sliding member.

30 Claims, 6 Drawing Sheets

U.S. PATENT DOCUMENTS

| | | |
|---|---|---|
| 4,925,448 | 5/1990 | Bazaral . |
| 4,950,245 | 8/1990 | Brown et al. . |
| 4,967,797 | 11/1990 | Manska . |
| 5,037,390 | 8/1991 | Raines et al. . |
| 5,163,554 | 11/1992 | Lampropoulos et al. . |
| 5,217,432 | 6/1993 | Rudzena et al. . |
| 5,247,966 | 9/1993 | Stevens et al. . |

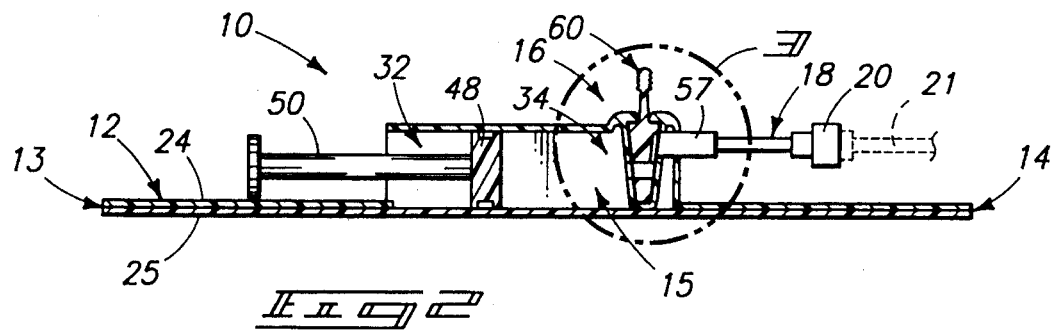

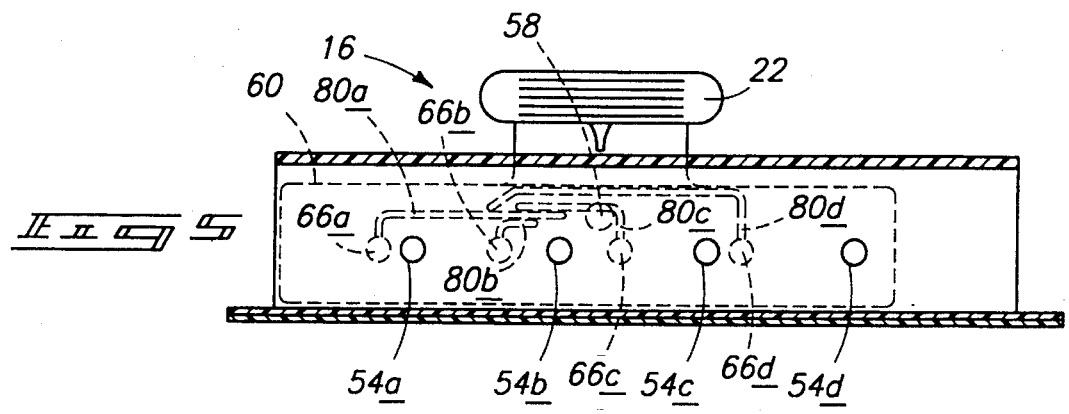
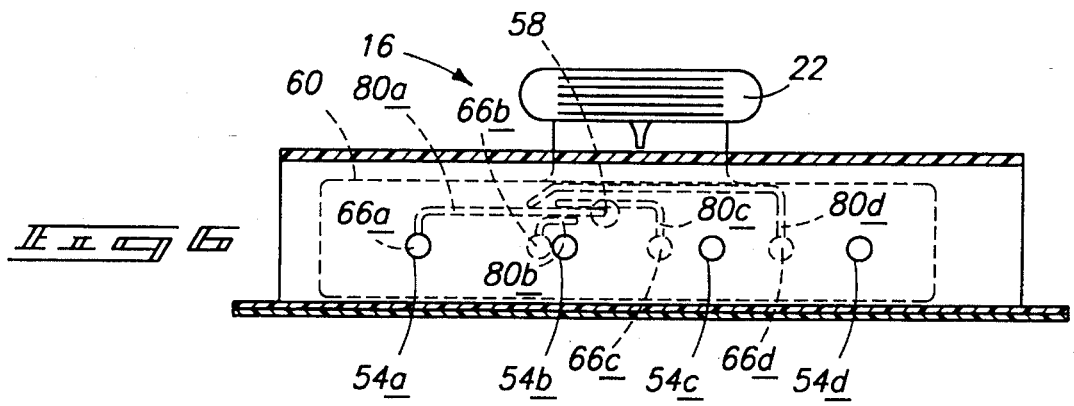
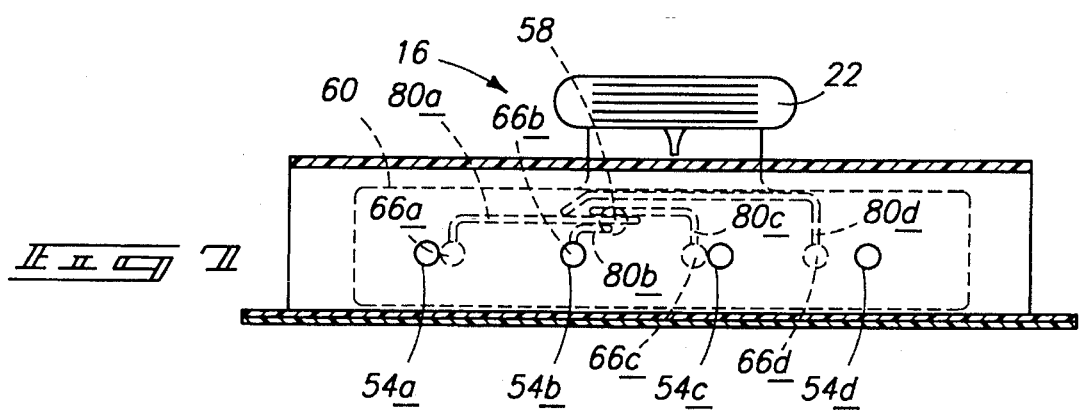

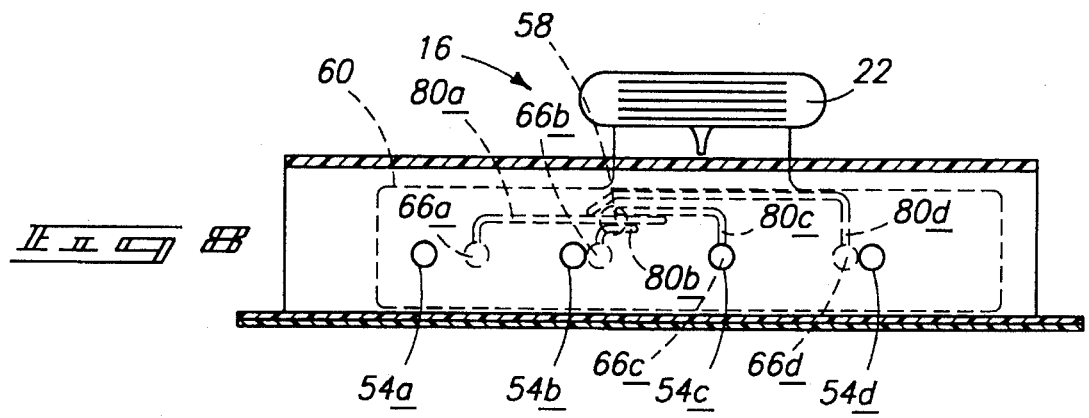
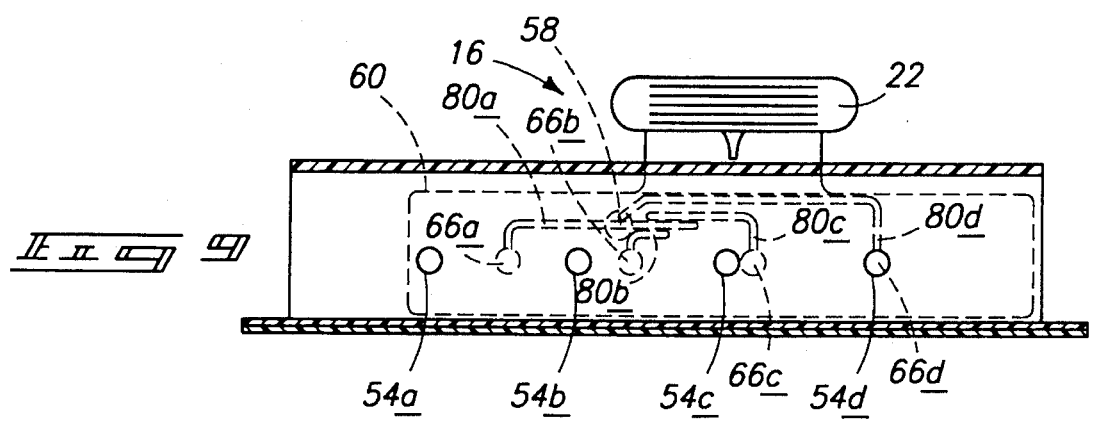

5,454,792

LINEAR SLIDE VALVE FOR CVC ACCESS

RELATED PATENT DATA

The patent resulted from a continuation-in-part patent application of U.S. patent application Ser. No. 08/187,632, filed Jan. 26, 1994, entitled "Catheter Access System and Method," now U.S. Pat. No. 5,411,485; and U.S. patent application Ser. No. 08/048,906, filed Apr. 19, 1993, entitled "Central Venous Catheter Access System And Syringes," now U.S. Pat. No. 5,308,322.

TECHNICAL FIELD

This invention relates to methods of and systems for accessing catheters which are invasively inserted relative to a patient's blood stream, and to the maintenance of such catheters.

BACKGROUND OF THE INVENTION

Catheters are commonly used to provide quick and direct access to a patient's blood stream. Commonly used catheters range from intravenous lines, which are used in a variety of routine situations, to central venous catheters (CVC), which are used in critical care situations. Catheter maintenance can be costly and troublesome, especially for all but the simplest short-term catheters such as those which access a patient's arm vein.

For example, a CVC is inserted by a surgical procedure in a vein very near the heart. A CVC is often left in place for a relatively long time. The skin entry point is kept covered by a carefully monitored dressing. Because of the direct nature of access to the blood stream, infection control when dealing with CVCs is of utmost importance. In most institutions, only registered nurses and doctors are allowed to perform procedures relating to CVC access.

A CVC includes one or more external access lumens, each having a terminus injection/withdrawal port which typically includes a needle-less connector such as a Luer-lok connector. To allow injection or withdrawal of fluids through the CVC, the connector is typically connected to a mating piece having a pierceable rubber membrane. Fluid transfer requires first cleaning the pierceable membrane with alcohol and/or Betadine, and then inserting a hypodermic syringe needle through the membrane to provide direct access to the blood stream. In some cases, syringes are connected directly to the CVC's connector without a needle, thereby eliminating the need for the pierceable membrane.

CVC access lumens can become clogged by clotted blood and fibrin. The access lumens are kept free from clots when not in use by injecting a heparin solution into them. This is commonly referred to as a heparin lock. Heparin is a protein material which acts as a blood anticoagulant. Before withdrawing a blood sample from a CVC, the heparin and the blood-containing heparin in the catheter is first withdrawn. Also, depending on the patient's condition and the type of catheter, it is sometimes desirable or necessary to withdraw heparin from the catheter before injecting a medication through the catheter.

There are significant risks associated with transferring fluid through a CVC. One risk is that of microbial infection. Another significant risk is that of air embolism. Both of these risks are potentially life-threatening and increase significantly with each access through the CVC access lumen, especially when such an access is by way of a needle and pierceable membrane. Compounding these risks is the fact that a single medication injection procedure or a single blood collection procedure can require four or more separate connections to the CVC access lumen, one for each separate fluid injection and withdrawal. In some cases, the CVC is used for medication injection or blood withdrawal as many as four to six times each day. Thus, as many as twenty-four CVC connections are required every day, with a corresponding number of opportunities for infection or air embolism. Over the period of a month, the CVC could present over 700 opportunities for life-threatening events to occur.

As an example, a simple medication injection procedure requiring heparin withdrawal includes the following steps. First, the pierceable membrane of the injection port must be cleaned with alcohol. The success of this step is highly dependent on the skill of the care-giver and is subject to mistakes caused by carelessness or inattentiveness. A needle of a waste blood withdrawal syringe is then inserted through the membrane. The syringe is operated to withdraw the heparin-containing blood from the CVC. Next, the catheter is flushed with a saline syringe. A medication syringe is then prepared, its needle inserted through the pierceable membrane, and medication injected into the CVC. Subsequently, another saline flush syringe is prepared and its contents injected to carry all the medication into the patient's blood stream. Finally, heparin is injected into the CVC through the pierceable membrane to re-establish the heparin lock. If all this is done quickly and correctly, the catheter will not clot, no air embolism will result, and the patient will not be infected.

Withdrawing or collecting blood requires similar steps. First, all heparin-containing blood is withdrawn from the CVC transfer lumen by injecting a needle through the pierceable membrane and withdrawing blood into a waste blood withdrawal syringe. After the heparin-containing blood is completely withdrawn from the catheter, the waste withdrawal needle is removed and a needle of another syringe is inserted to withdraw non-heparin contaminated blood. Then a normal saline flush is injected, followed by a heparin injection with yet another needle and syringe to establish a heparin lock.

As is apparent from the above discussion, another problem with standard CVC access procedures is that the various solutions and syringes needed to access a CVC are supplied separately. A nurse must often collect these materials from different places. This can be a costly and time consuming process. Furthermore, even after proper equipment is found it equipment is often not designed to work together as a system.

In part because of this, CVC procedures are performed only by registered nurses or doctors, with the procedure consuming a large quantity of their valuable time. The patient and other care-givers are often forced to remain idle while waiting for the qualified persons to find time to provide the catheter access service.

As an additional complication, access to a CVC by needle gives rise to a potential source of injury and infection to the care-giver through contact with the needle. This is particularly important when the patient being treated has a dangerous infection, such as HIV or hepatitis. Often, the care-giver and patient are unaware that an infection is present.

In addition to CVC maintenance and operation as described above, it can be highly desirable in emergency situations to get a plurality of medications quickly into a patient's bloodstream through a CVC or other catheter. It would be highly desirable in such situations for the care-giver to have a catheter access system which facilitates multiple accesses to the catheter.

Our U.S. Pat. No. 5,308,322, formerly U.S. patent application Ser. No. 08/048,906, and our U.S. Pat. No. 5,411,485, formerly U.S. patent application Ser. No. 08/187,632, are hereby incorporated by reference.

BRIEF DESCRIPTION OF THE DRAWINGS

FIG. 2 is a sectional side view taken along line 2—2 of FIG. 1.

FIG. 3 is an enlarged and exploded sectional side view showing the circled portion of FIG. 2.

FIG. 4 is an enlarged forward end view of a sliding member as shown in FIGS. 1–3.

FIGS. 5–9 are diagrammatic sectional views taken along line 5—5 of FIG. 1, showing a slide valve in accordance with the invention at various sequential positions.

DETAILED DESCRIPTION OF THE PREFERRED EMBODIMENTS

Figure 1:
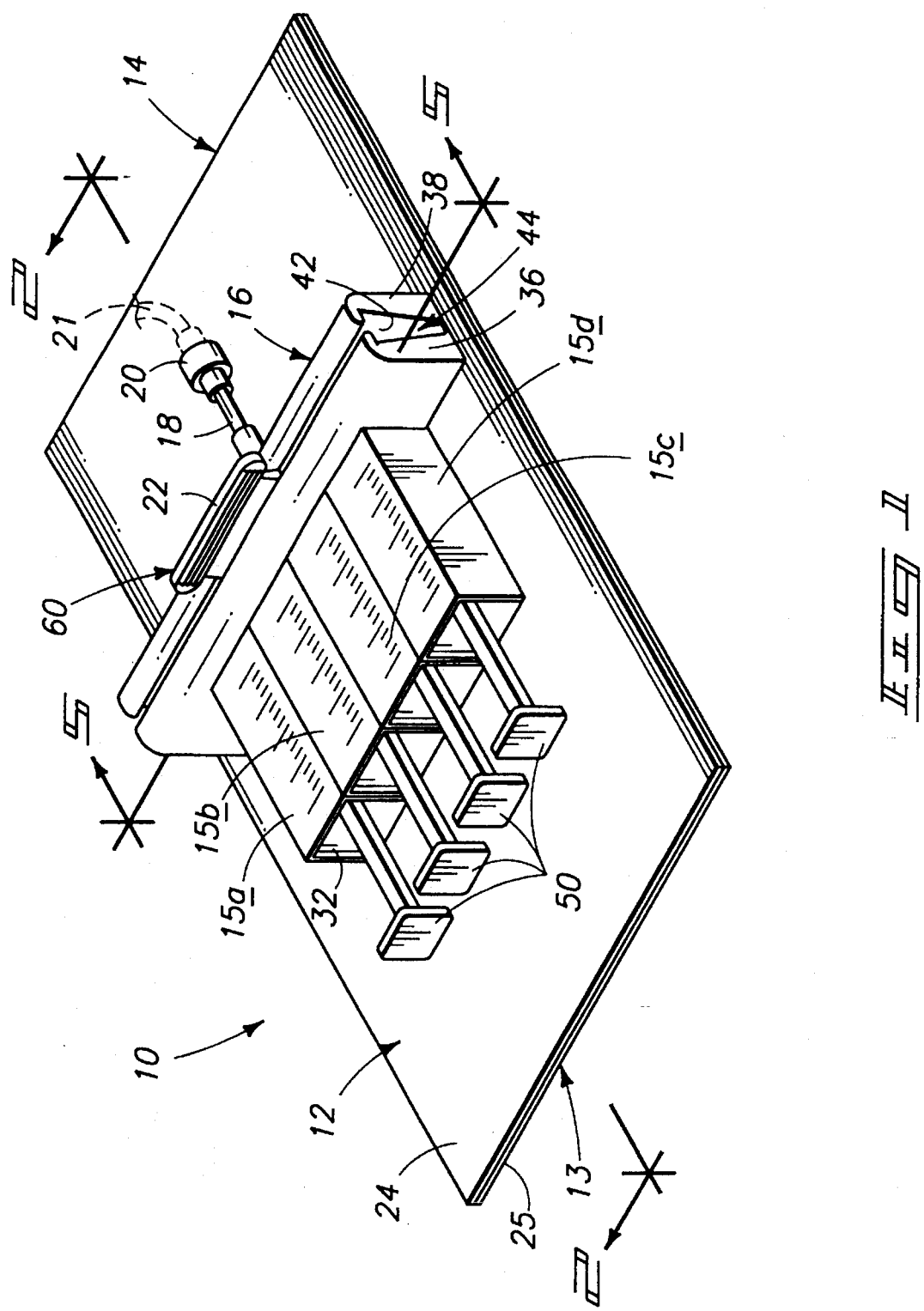
FIG. 1 is a top perspective view of a preferred embodiment catheter access system in accordance with the invention.

This disclosure of the invention is submitted in furtherance of the constitutional purposes of the U.S. Patent Laws "to promote the progress of science and useful arts." U.S. Constitution, Article 1, Section 8.

In accordance with one aspect of the invention, a catheter access system comprises:

a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member;

the collective sliding member passageways defining a series of mutually exclusive courses through the sliding member from the inlet ports to the outlet port to restrict mixing of fluids from different syringes.

FIGS. 1–4 show a catheter access system in accordance with a preferred embodiment of the invention, indicated generally by reference numeral 10. Catheter access system 10 includes a rectangular sterile supporting sheet or base 12 which extends in a longitudinal direction from a rearward end 13 to a forward end 14. Access system 10 also includes a plurality of syringes or syringe barrels 15a–15d (referred to collectively as syringes 15) and a syringe selection slide valve 16, all of which are mounted integrally to base 12. Slide valve 16 is positioned toward forward end 14 of supporting base 12 forwardly from syringes 15.

A slide valve outlet tube or port 18 extends from slide valve 16 toward base forward end 14. Valve outlet tube 18 has a Luer-lok connector 20 at its outer end to facilitate needle-less connection between access system 10 and a catheter access line 21, such as a central venous catheter in a patient. Slide valve 16 has a handle or knob 22 which can be positioned or slid by a care-giver to provide fluid communication between a selected one of syringes 15 and slide valve outlet tube 18.

Supporting base 12 is formed by laminated first and second (upper and lower) base sheets 24 and 25. Upper base sheet 24 is integrally molded to form a plurality of generally rectangular syringe channels in a thin sheet of medically-approved plastic such as high-density polypropylene, using common blow-molding or injection processes. The syringe channels project upwardly or outwardly from upper sheet 24, having rectangular transverse cross sections and lengths which are formed along upper sheet 24. The channels are open toward the bottom or under side of upper sheet 24. The channels are formed to adjoin each other in side-by-side and parallel relationship. They extend from rearward ends 32 to forward ends 34. After molding, rearward ends 32 are opened by cutting them away for plunger insertion. Forward ends 34 remain closed, but for fluid passages which are described below.

Referring to FIG. 3, upper base sheet 24 is further molded to form first and second opposed and elongated slide valve walls 36 and 38. Slide valve walls 36 and 38 are upstanding ridges molded in upper sheet 24 to project and extend upwardly therefrom. They are open toward the bottom of upper sheet 24. The channels which form syringes 15 intersect first slide valve wall 36. The opposed slide valve walls define and form first and second inner wall or valley surfaces 40 and 42 which in turn form a longitudinal and upwardly-open synclinal valley 44 therebetween. Base sheet 24 forms a flat valley floor 45 between valley walls 36 and 38. Retaining lips 46 are formed along the tops of the slide valve walls.

Lower base sheet 25 is preferably a planar sheet of plastic, such as medically-approved high-density polypropylene. Access system 10 is formed by laminating planar lower sheet 25 beneath upper sheet 24. This closes the syringe channels formed by upper sheet 24 to form syringes 15. An independently operable syringe plunger 48 (FIG. 2) is slidably received within each syringe channel. Each syringe plunger 48 is preferably rectangular to fit snugly and sealingly within its syringe barrel. An elongated handle 50 extends from each plunger 48, through open rearward end 32 of the corresponding syringe.

A plurality of apertures 52, formed through first valley wall 36, form both syringe outlet apertures and slide valve inlet ports. They are referred to in the following discussion as slide valve inlet ports. A valve inlet port 52 corresponds to each syringe 15 and extends from the interior of said syringe, through first valley wall 36, and into valley 44. The inlet ports form corresponding inlet port orifices 54 in first valley surface 40. Slide valve outlet port 18 includes an enlarged terminating conduit 57 which extends through second valley wall 38 and into valley 44, forming an outlet port orifice 58 in second wall surface 42.

While syringes 15 are integrally formed with supporting base 12 in the preferred embodiment, an access system in accordance with the invention could also use non-integrally formed syringes such as conventional cylindrical plastic syringes. Such syringes would be connected with their outlet apertures in fluid communication with slide valve inlet ports 52, possibly with mating Luer-loc connectors. In some cases it might be desirable for one or more of the syringes to be removable, such as when one of the syringes is used to withdraw a blood sample, or one of the syringes is supplied just prior to use to inject a selected medication.

Slide valve 16 of access system 10 includes an elongated sliding member 60 which is received for linear sliding movement along a longitudinal axis within valley 44. Sliding member 60 is received within slide valve walls 36 and 38 between slide valve inlet ports 52 and slide valve outlet port 18. Sliding member 60 is movable between a plurality of discrete longitudinal positions to individually select slide valve inlet ports 52 for connection to slide valve outlet port 18. It is retained in valley 44 by retaining lips 46. Handle 22 protrudes upwardly from between retaining lips 46.

Sliding member 60 is preferably a wedge-shaped solid body which is complementary in shape to synclinal valley 44 so that it fits tightly therein while still being capable of longitudinal sliding motion. It can be inexpensively mass-produced by injection molding a medically-approved plastic. Member 60 has first and second opposed sliding surfaces 62 and 64 which are in sliding abutment with surfaces 40 and 42, respectively, of valley walls 36 and 38; and with inlet and outlet orifices 54 and 58, respectively.

As best shown in FIG. 4, sliding member 60 has a plurality of sliding member passageways 66 formed therethrough from first sliding surface 62 to second sliding surface 64. One passageway 66 corresponds to each of inlet ports 52 and to each of syringes 15. The passageways are labelled with suffices a–d to indicate their correspondence with particular syringes 15a–15d. The passageways are located so that different passageways 66 connect between corresponding slide valve inlet ports 52 and slide valve outlet port 18 at different longitudinal positions of sliding member 60.

More specifically, each passageway 66 has a first open termination 70 (FIG. 3) along first sliding surface 62 for selective communication with a corresponding inlet port 52. Each passageway 66 also has a second open termination 72 along second sliding surface 64 to communicate with outlet tube 58.

First open terminations 70 are simply the circular openings of passageways 66 along first sliding surface 62. First open terminations 70 are positioned so that a single one of first open terminations 70 is aligned with a corresponding one of inlet port orifices 54 at a corresponding one of the discrete longitudinal positions of sliding member 60. Said single one of first open terminations 70 is sealed by first valley surface 40 at other discrete longitudinal positions of sliding member 60.

Such selective alignment is accomplished in the preferred embodiment by spacing inlet port orifices 54 longitudinally from each other along first valley surface 40 at a first regular pitch or spacing. Passageways 66 and first open terminations 70 are spaced longitudinally from each other along first sliding surface 62 of sliding member 60 at a second regular pitch or spacing. The first and second regular pitches are different from each other, so that no more than a single one of first open terminations 70 is aligned with an inlet port orifice 54 at any single discrete longitudinal position of elongated sliding member 60. The first pitch is greater than the second pitch in the preferred embodiment.

Second open terminations 72 preferably comprise elongated open channels 80 formed in and along second sliding surface 64 of sliding member 60. The open channels are positioned against second valley surface 42, so that valley wall 38 seals against the channels. Each of the second open terminations is positioned to align with outlet port orifice 58 at at least one of the discrete longitudinal positions of elongated sliding member 60. More specifically, the channel associated with each passageway 66 is positioned so that it aligns with outlet port orifice 58 when the passageway's first open termination 70 is aligned with its corresponding inlet port orifice 54. This particular arrangement of passageways and channels defines an exclusive course for fluid communication between the selected slide valve inlet port and the slide valve outlet port to restrict mixing of fluids from different syringes. When an individual syringe is selected by properly positioning sliding member 60, there is only a single course for fluid from the selected syringe to outlet port 18. This course does not cross the course used by the fluid of any other syringe when it is selected. While more than one of channels 80 may be aligned with outlet port aperture 58 at any single sliding member position, fluid flow into or through non-selected passageways is prevented by the sealing of first valley surface 40 against those passageways' first open terminations 70.

FIGS. 5–9 illustrate the selective and sequential alignment of inlet port orifices 54 and passageways 66 resulting from positioning sliding member 60. The various orifices, ports, and passageways are indicated by reference numeral suffixes a–d, corresponding to syringes 15a–15d, respectively.

In FIG. 5, sliding member 60 is shown in an initial "0", "off", or sealed position, in which none of inlet port orifices 54 are aligned with a sliding member passageway 66. Each of slide valve inlet ports 52 is sealed off at its orifice 54 by the abutting first sliding surface 62 of sliding member 60.

FIG. 6 shows a first or "1" position of sliding member 60 in which a first, single inlet port orifice 54a aligns with a first, single corresponding sliding member passageway 66a. In this position, a first channel 80a, associated with first passageway 66a, is aligned for fluid communication with outlet port orifice 58. Moving sliding member 60 to its first position therefore establishes fluid communication from syringe 15a to outlet port 18.

FIG. 7 shows a second or "2" position in which a second, single inlet port orifice 54b aligns with a second, single corresponding sliding member passageway 66b. In this position, a second channel 80b, associated with second passageway 66b, is aligned for fluid communication with outlet port orifice 58. Moving sliding member 60 to its second position therefore establishes fluid communication from syringe 15b to outlet port 18.

FIGS. 8 and 9 show third and fourth positions of sliding member 60, in which fluid communication is established between third and fourth syringes 15c and 15d, respectively, and outlet port 18.

The construction and fabrication methods described above should be inexpensive to implement. Most of the components are formed by upper sheet 24. For instance, the syringes, the slide valve walls, and internal individual fluid passages are formed by the upper sheet. This formation, in addition to being inexpensive, provides a planar base which can be conveniently taped to a patient or clipped to a patient's gown during catheter access operations. Furthermore, at least one of the laminated upper and lower sheets which forms supporting base 12 preferably has a longitudinal extent or dimension which is greater than a combined longitudinal extent of the syringes and slide valve. When the access system is packaged in a sterile condition, base 12 provides a sterile field underlying the access components, facilitating sterile connection procedures. Taping the base to a patient greatly simplifies the task of maintaining the cleanliness and sterility of components during catheter access.

The above-described catheter access system 10 can be used either to inject medication or other solutions into patients through a CVC or other catheter, or to withdraw a patient's blood through the catheter. In either case, the sequence of steps required to accomplish the desired fluid transfers to or from the patient can be accomplished without the numerous and sequential independent connections previously required. As an example, steps involved in administering a patient medication where heparin removal is first required are described below. Catheter access system 10 is preferably provided in a pre-filled condition by or for the care-giver, ready for immediate connection to a CVC access lumen in a patient, for example. By way of example only, a first syringe 15a would not be pre-filled, but would instead be utilized as a fluid withdrawal syringe. A second syringe 15b would be pre-filled with a desired medication. Alternatively, second syringe 15b could be a non-integral syringe which would be filled and connected to access system 10 during or just before use. A third syringe 15c would be pre-filled with a flushing saline, and a fourth syringe 15d would be pre-filled with heparin prior to any access to the catheter. Also, the internal volume of the various fluid conduits and passageways of the system, such as outlet tube 18 and fluid passageways 66, would preferably be initially pre-filled with saline to eliminate air.

With connector 20 of the system connected with the patient's catheter, handle 22 is slid to a position corresponding to first syringe 15a. The plunger 50 of syringe 15a is then withdrawn to withdraw heparin-containing blood from the patient's catheter. Handle 22 is then slid to select second syringe 15b. Medication from syringe 15b is pushed into the catheter and patient. Handle 22 is slid again to select third syringe 15c. Saline is then pushed in to clear all medication from the catheter into the patient, leaving saline in the catheter. Handle 22 is slid one more time to select fourth syringe 15d, and the plunger of syringe 15d is depressed to establish a heparin lock within the patient's catheter.

Appropriate indicia are provided on slide valve 16 to indicate proper handle positions and to prompt the care-giver to carry out the administration steps in the correct sequence. Valve positions are preferably arranged so that sliding handle 22 in one direction, to sequential positions, will facilitate the desired order of steps.

The above system could, of course, be utilized in other manners for administering one or more medications to a patient's catheter or for withdrawing blood for analysis from a catheter, as will be appreciated by medical personnel of skill in the art. By way of example only, the above system could be utilized in emergency situations where a typical sequence of multiple drugs might need to be administered through a patient's catheter apart from any association with a catheter having a heparin lock. In such instances, many or all of the apparatus syringes might be provided with medication, as opposed to saline.

Furthermore, it is contemplated that multiple access systems might be utilized in combination or series in emergency situations. For such use, it might be desirable to add a fifth valve position and inlet port, and a corresponding auxiliary mating connector for connection to another, upstream syringe or access system. This would allow sequential emergency medications from different access systems to be quickly administered without requiring disconnection from the patient's CVC.

Figure 10:
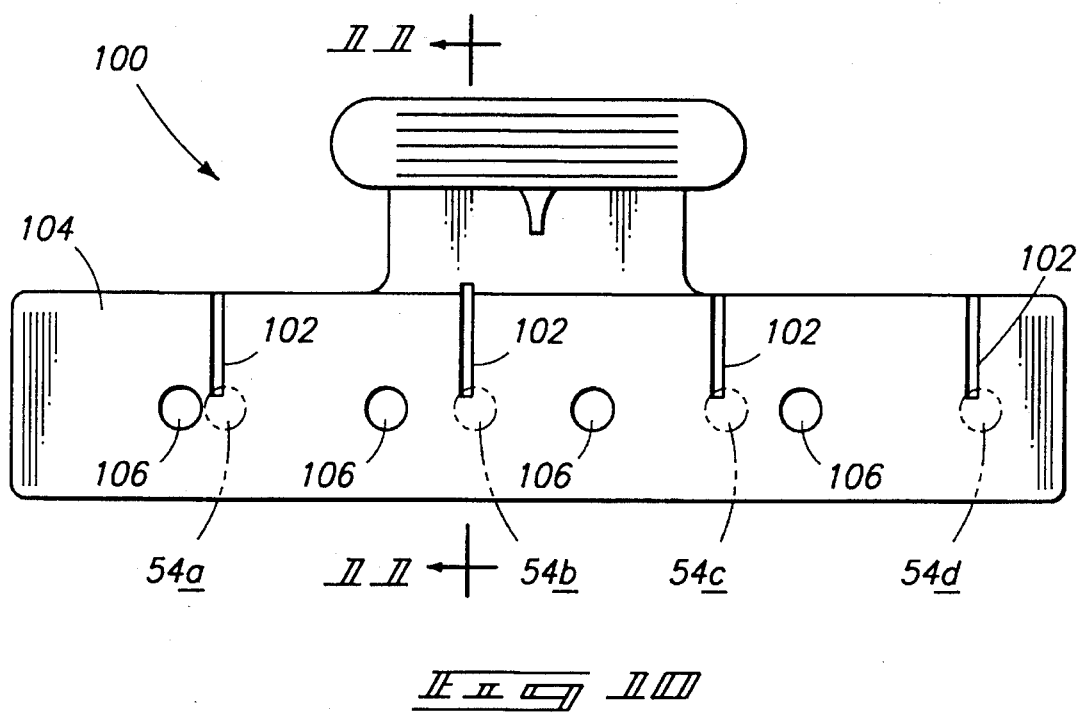
FIG. 10 is an enlarged rearward end view of an alternative sliding member in accordance with the invention.
Figure 11:
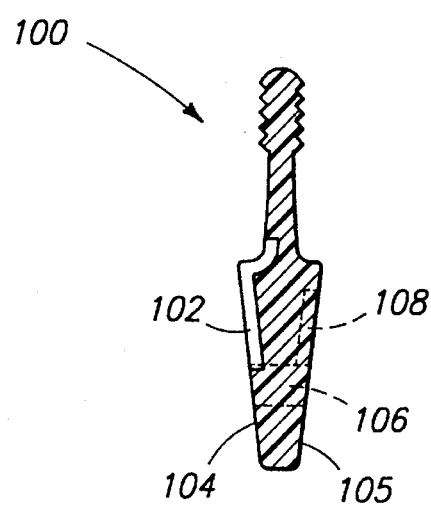
FIG. 11 is a sectional side view taken along line 11—11 of FIG. 10.

FIGS. 10 and 11 illustrate an additional slider member feature which could advantageously be incorporated in the access system described above. FIGS. 10 and 11 show an alternatively constructed sliding member 100 which is largely identical to sliding member 60 described above. Sliding member 100 has internal passageways 106, similar to passageways 66 described above, first and second sliding surfaces 104 and 105, and passageway channels 108 on second sliding surface 105. However, sliding member 100 has additional vent passageways for venting connected syringes prior to fluid administration. More specifically, sliding member 100 has four vent channels 102 formed vertically along its first sliding surface 104. Vent channels 102 are positioned to simultaneously align with all of inlet port orifices 54 at a single position of sliding member 100, and to extend upward therefrom to a point above first valley wall 36. Inlet port orifices 54 are shown in dashed lines in FIG. 10 to indicate this alignment. Vent channels 102 define a sliding member syringe vent position, preferably between the "0" and "1" positions described above. With sliding member 100 in the vent position, the vents connect from the slide valve inlet ports to ambient atmosphere, thus allowing air to be expelled from any connected syringes prior to actual CVC injections. Such a feature would be especially useful in a CVC access device having non-integral syringes, or syringes which are filled just prior to use.

Figure 12:
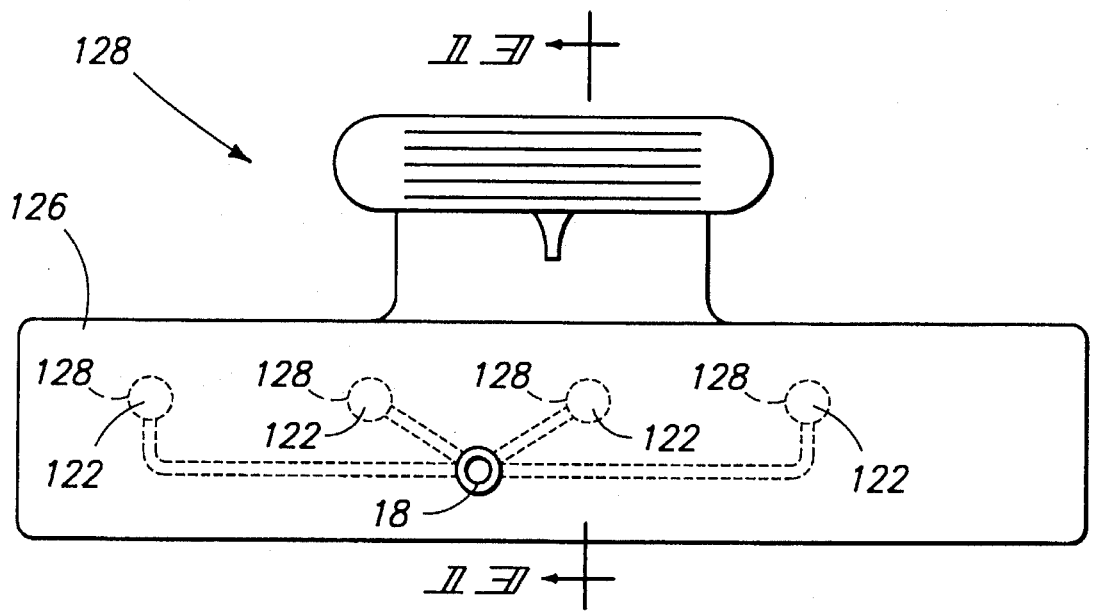
FIG. 12 is an enlarged forward end view of another alternative sliding member in accordance with the invention.
Figure 13:
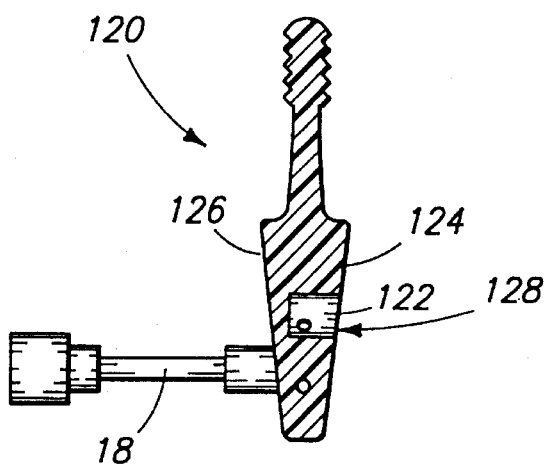
FIG. 13 is a sectional side view taken along line 13—13 of FIG. 12.

FIGS. 12 and 13 illustrate yet another alternative construction of a sliding member, designated by reference numeral 120. Sliding member 120 has internal passageways 122, similar to passageways 66 described above, first and second sliding surfaces 124 and 126, and first open terminations 128 on first sliding surface 124. Rather than having open channels on second sliding surface 126, however, outlet tube 18 is physically connected to and extends from second sliding surface 126 of sliding member 120. Passageways 122 each communicate through sliding member 120 with outlet tube 18, being formed to converge at outlet port 18 from first open terminations 128. A slot (not shown) is provided in second valley wall 38 of slide valve 16. Outlet tube 18 extends through the slot, which allows sliding member 120 and its connected outlet tube 18 to slide longitudinally within valley 44.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A catheter access system comprising:
    a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member; and the collective sliding member passageways defining a series of mutually exclusive courses through the sliding member from the inlet ports to the outlet port to restrict mixing of fluids from different syringes, the inlet ports forming inlet orifices which are in sliding engagement with the elongated sliding member, the inlet orifices being longitudinally spaced from each other at a first regular pitch, the sliding member passageways being longitudinally spaced from each other at a second regular pitch that is different from the first regular pitch.

2. A catheter access system comprising:

a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member;

the collective sliding member passageways defining a series of mutually exclusive courses through the sliding member from the inlet ports to the outlet port to restrict mixing of fluids from different syringes;

the slide valve outlet port forms a corresponding outlet port orifice;

the elongated sliding member has a sliding surface which is in sliding abutment with the outlet port orifice;

the sliding member passageways have open terminations along the sliding member sliding surface, each such open termination being positioned to align with the outlet port orifice at at least one of the discrete longitudinal positions of the elongated sliding member;

wherein the open terminations comprise elongated channels formed in the sliding member along the sliding member sliding surface and in sliding abutment with the outlet port orifice.

3. A catheter access system comprising:

a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member;

the collective sliding member passageways defining a series of mutually exclusive courses through the sliding member from the inlet ports to the outlet port to restrict mixing of fluids from different syringes;

the slide valve outlet port forms a corresponding outlet port orifice;

the elongated sliding member has a sliding surface which is in sliding abutment with the outlet port orifice;

the sliding member passageways have open terminations along the sliding member sliding surface, each such open termination being positioned to align with the outlet port orifice at at least one of the discrete longitudinal positions of the elongated sliding member;

the slide valve inlet ports form corresponding inlet port orifices, the slide valve outlet port forming a corresponding outlet port orifice;

the elongated sliding member has first and second sliding surfaces, the first sliding surface being in sliding abutment with the inlet port orifices, the second sliding surface being in sliding abutment with the outlet port orifice;

the sliding member passageways extend through the elongated sliding member from the first sliding surface to the second sliding surface, the passageways having first and second open terminations along the first and second sliding surfaces, respectively;

each of the first open terminations being positioned to align with a corresponding one of the inlet port orifices at a corresponding one of the discrete longitudinal positions of the elongated sliding member;

each of the second open terminations being positioned to align with the outlet port orifice at at least one of the discrete longitudinal positions of the elongated sliding member;

wherein the second terminations comprise elongated channels formed along the second sliding surface.

4. A catheter access system comprising:

a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member; and the collective sliding member passageways defining a series of mutually exclusive courses through the sliding member from the inlet ports to the outlet port to restrict mixing of fluids from different syringes, a wall surface formed by at least one of the elongated slide valve walls, the slide valve outlet port forming a corresponding outlet port orifice in the wall surface;

the elongated sliding member having a sliding surface which is in sliding abutment with the wall surface and the outlet port orifice;

the sliding member passageways having open terminations along the sliding member sliding surface, each such open termination being positioned to align with the outlet port orifice at at least one of the discrete longitudinal positions of the elongated sliding member;

wherein the open terminations comprise elongated channels formed along the sliding member sliding surface.

5. A catheter access system comprising:

a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member; and the collective sliding member passageways defining a series of mutually exclusive courses through the sliding member from the inlet ports to the outlet port to restrict mixing of fluids from different syringes;

first and second wall surfaces formed by the elongated slide valve walls, the slide valve inlet ports forming corresponding inlet port orifices in the first wall surface, the slide valve outlet port forming a corresponding outlet port orifice in the second wall surface;

the elongated sliding member having first and second sliding surfaces, the first sliding surface being in sliding abutment with the first wall surface and the inlet port orifices, the second sliding surface being in sliding abutment with the second wall surface and the outlet port orifice;

the sliding member passageways extending through the elongated sliding member from the first sliding surface to the second sliding surface, the passageways having first and second open terminations along the first and second sliding surfaces, respectively;

each of the first open terminations being positioned to align with a corresponding one of the inlet port orifices at a corresponding one of the discrete longitudinal positions of the elongated sliding member and being positioned to be sealed by the first wall surface at other discrete longitudinal positions of the elongated sliding member;

each of the second open terminations being positioned to align with the outlet port orifice at at least one of the discrete longitudinal positions of the elongated sliding member;

wherein the second terminations comprise elongated channels formed along the second sliding surface.

6. A catheter access system comprising:

a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member; and the collective sliding member passageways defining a series of mutually exclusive courses through the sliding member from the inlet ports to the outlet port to restrict mixing of fluids from different syringes;

wherein one of the discrete longitudinal positions of the elongated sliding member is a syringe vent position, the elongated sliding member having vent passageways which are positioned to connect from the slide valve inlet ports to ambient atmosphere when the elongated sliding member is in its syringe vent position.

7. A catheter access system comprising:

a slide valve, the slide valve having elongated slide valve walls, the slide valve walls having a plurality of slide valve inlet ports extending therethrough and having a slide valve outlet port extending therethrough;

a plurality of syringes having syringe outlet apertures in fluid communication with the slide valve inlet ports;

the slide valve including an elongated sliding member which is received for linear sliding movement along a longitudinal axis within the slide valve walls between the slide valve inlet ports and the slide valve outlet port, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member; and the collective sliding member passageways defining a series of mutually exclusive courses through the sliding member from the inlet ports to the outlet port to restrict mixing of fluids from different syringes;

wherein the outlet port comprises an outlet tube physically connected to and extending from the elongated sliding member and moveable therewith, each of the passageways communicating through the elongated sliding member with the outlet tube.

8. A catheter access system comprising:

an integrally molded base sheet forming first and second opposed slide valve walls extending therefrom, the slide valve walls forming an upwardly-open longitudinal valley therebetween;

a plurality of slide valve inlet ports extending through the first slide valve wall;

a slide valve outlet port extending through the second slide valve wall;

a plurality of syringes mounted on the integrally-molded base sheet for fluid communication with the slide valve inlet ports;

an elongated sliding member which is received for linear sliding movement within the longitudinal valley formed by the first and second slide valve walls, the elongated sliding member being movable between a plurality of discrete longitudinal positions to individually select slide valve inlet ports for connection to the slide valve outlet port;

the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member.

9. A catheter access system as recited in claim 8, wherein the collective sliding member passageways define a series of mutually exclusive courses through the sliding member from the inlet ports to the outlet port to restrict mixing of fluids from different syringes.

10. A catheter access system as recited in claim 8, the inlet ports forming inlet orifices which are in sliding engagement with the elongated sliding member, the inlet orifices being longitudinally spaced from each other at a first regular pitch along the first slide valve wall, the sliding member passageways being longitudinally spaced from each other at a second regular pitch that is different from the first regular pitch.

11. A catheter access system as recited in claim 8, the outlet port forming an output orifice along the second slide valve wall which is in sliding engagement with the elongated sliding member, each of the sliding member passageways being positioned to align with the outlet port orifice at at least one of the discrete longitudinal positions of the elongated sliding member.

12. A catheter access system as recited in claim 8 and further comprising retaining lips formed along the opposed slide valve walls to retain the sliding member within the longitudinal valley.

13. A catheter access system as recited in claim 8 wherein the longitudinal valley is synclinal, the elongated sliding member being wedge-shaped to fit within the longitudinal valley.

14. A catheter access system as recited in claim 8 wherein the longitudinal valley is synclinal, the elongated sliding member being a solid wedge-shaped body, the sliding member passageways being formed therethrough.

15. A catheter access system as recited in claim 8 and further comprising:

a valley surface formed by the first slide valve wall, the slide valve inlet ports forming corresponding inlet port orifices in the valley surface;

the elongated sliding member having a sliding surface which is in sliding abutment with the valley surface and the inlet port orifice;

the sliding member passageways having open terminations along the sliding member sliding surface, each such open termination being positioned to align with a corresponding one of the inlet port orifices at a corresponding one of the discrete longitudinal positions of the elongated sliding member and being positioned to be sealed by the valley surface at other discrete longitudinal positions of the elongated sliding member.

16. A catheter access system as recited in claim 15 wherein:

the inlet port orifices are spaced longitudinally from each other along the valley surface at a first regular pitch;

the open terminations are spaced longitudinally from each other along the sliding member sliding surface at a second regular pitch;

the first and second regular pitches are different from each other so that no more than a single one of the open terminations is aligned with an inlet port orifice at any single discrete longitudinal position of the elongated sliding member.

17. A catheter access system as recited in claim 8 and further comprising:

a valley surface formed by the second slide valve wall, the slide valve outlet port forming a corresponding outlet port orifice in the valley surface;

the elongated sliding member having a sliding surface which is in sliding abutment with the valley surface and the outlet port orifice;

the sliding member passageways having open terminations along the sliding member sliding surface, each such open termination being positioned to align with the outlet port orifice at at least one of the discrete longitudinal positions of the elongated sliding member.

18. A catheter access system as recited in claim 17 wherein the open terminations comprise elongated channels formed along the sliding member sliding surface against the valley surface, the valley surface sealing against the elongated channels.

19. A catheter access system as recited in claim 8 and further comprising:

first and second opposed valley surfaces formed by the opposed slide valve walls;

the slide valve inlet ports forming corresponding inlet port orifices in the first valley surface, the slide valve outlet port forming a corresponding outlet port orifice in the second valley surface;

the elongated sliding member being having first and second sliding surfaces, the first sliding surface being in sliding abutment with the first valley surface and the inlet port orifices, the second sliding surface being in sliding abutment with the second valley surface and the outlet port orifice;

the sliding member passageways extending through the elongated sliding member from the first sliding surface to the second sliding surface, the passageways having first and second open terminations along the first and second sliding surfaces, respectively;

each of the first open terminations being positioned to align with a corresponding one of the inlet port orifices at a corresponding one of the discrete longitudinal positions of the elongated sliding member and being positioned to be sealed by the first valley surface at other discrete longitudinal positions of the elongated sliding member;

each of the second open terminations being positioned to align with the outlet port orifice at at least one of the discrete longitudinal positions of the elongated sliding member.

20. A catheter access system as recited in claim 19 wherein the open terminations comprise elongated channels formed along the sliding member sliding surface against the second valley surface, the second valley surface sealing against the elongated channels.

21. A catheter access system as recited in claim 8 wherein one of the discrete longitudinal positions of the elongated sliding member is a syringe vent position, the elongated sliding member having vent passageways which are positioned to connect from the slide valve inlet ports to ambient atmosphere when the elongated sliding member is in its syringe vent position.

22. A catheter access system as recited in claim 8 wherein the outlet port comprises an outlet tube physically connected to and extending from the elongated sliding member, each of the passageways communicating through the elongated sliding member with the outlet tube.

23. A catheter access system comprising:

a supporting base;

first and second opposed slide valve walls extending from the supporting base, the opposed slide valve walls forming a longitudinal valley therebetween;

a plurality of slide valve inlet ports extending through the first slide valve wall to form corresponding inlet port orifices, the inlet port orifices being spaced longitudinally from each other at a first regular pitch;

a slide valve outlet port extending through the second slide valve wall to form a corresponding outlet port orifice;

a plurality of syringes mounted on the supporting base for fluid communication with the slide valve inlet ports;

an elongated sliding member which is received for linear sliding movement within the longitudinal valley, the elongated sliding member being movable between a plurality of discrete longitudinal positions to individually select slide valve inlet ports for connection to the slide valve outlet port;

the elongated sliding member having first and second sliding surfaces, the first sliding surface being in sliding abutment with the first slide valve wall and the inlet port orifices, the second sliding surface being in sliding abutment with the second slide valve wall and the outlet port orifice;

the elongated sliding member having a plurality of sliding member passageways extending therethrough, the passageways having first open terminations along the first sliding member sliding surface corresponding to the slide valve inlet ports, the passageways having second open terminations along the second sliding member sliding surface to communicate with the outlet port orifice;

the first open terminations being spaced longitudinally from each other along the sliding member sliding surface at a second regular pitch;

the first and second regular pitches being different from each other, a single one of the first open terminations being aligned with one of the inlet port orifices at different discrete longitudinal positions of the elongated sliding member.

24. A catheter access system as recited in claim 23 and further comprising retaining lips formed along the opposed slide valve walls to retain the sliding member within the longitudinal valley.

25. A catheter access system as recited in claim 23 wherein the longitudinal valley is synclinal, the elongated sliding member being wedge-shaped to fit within the longitudinal valley, the sliding member passageways being formed through the elongated sliding member.

26. A catheter access system as recited in claim 23 wherein the outlet port comprises an outlet tube connected to and extending from the elongated sliding member, each of the passageways communicating through the elongated sliding member with the outlet tube.

27. A catheter access system as recited in claim 23 wherein the open terminations comprise elongated channels formed along the second sliding surface of the sliding member against the second slide valve wall, the second slide valve wall sealing against the elongated channels.

28. A catheter access system comprising:

a slide valve having first and second opposed slide valve walls, the slide valve walls forming an upwardly-open longitudinal valley therebetween;

a plurality of slide valve inlet ports extending through the first slide valve wall;

a slide valve outlet port extending through the second slide valve wall;

a plurality of syringes mounted on the integrally-molded base sheet for fluid communication with the slide valve inlet ports;

an elongated sliding member which is received for linear sliding movement within the longitudinal valley formed by the first and second slide valve walls, the elongated sliding member being movable between a plurality of discrete longitudinal positions to individually select slide valve inlet ports for connection to the slide valve outlet port; and the elongated sliding member having a plurality of sliding member passageways corresponding to the slide valve inlet ports, each of the sliding member passageways connecting between its corresponding slide valve inlet port and the slide valve outlet port at a corresponding different discrete longitudinal position of the elongated sliding member; and the longitudinal valley being synclinal, the elongated sliding member being wedge-shaped to fit within the longitudinal valley.

29. A catheter access system as recited in claim 28 and further comprising retaining lips formed along the opposed slide valve walls to retain the sliding member within the longitudinal valley.

30. A catheter access system as recited in claim 28 wherein the outlet port comprises an outlet tube physically connected to and extending from the elongated sliding member and moveable therewith, each of the passageways communicating through the elongated sliding member with the outlet tube.

* * * * *